US007818060B2

(12) United States Patent  (10) Patent No.: US 7,818,060 B2
Torgerson  (45) Date of Patent: Oct. 19, 2010

(54) DETERMINATION OF STIMULATION OUTPUT CAPABILITIES THROUGHOUT POWER SOURCE VOLTAGE RANGE

(75) Inventor: Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 121 days.

(21) Appl. No.: 12/362,198

(22) Filed: Jan. 29, 2009

(65) Prior Publication Data

US 2010/0114252 A1  May 6, 2010

Related U.S. Application Data

(60) Provisional application No. 61/110,453, filed on Oct. 31, 2008.

(51) Int. Cl.
 *A61N 1/00* (2006.01)
(52) U.S. Cl. ..................................................... 607/29
(58) Field of Classification Search .................. 363/60; 607/2, 29, 72, 63
See application file for complete search history.

(56) References Cited

U.S. PATENT DOCUMENTS

| 4,606,350 | A | 8/1986 | Frost |
| 5,065,083 | A | 11/1991 | Owens |
| 5,453,698 | A | 9/1995 | Williams et al. |
| 5,744,931 | A | 4/1998 | Arai et al. |
| 6,115,272 | A | 9/2000 | Pasternak |
| 6,748,273 | B1 | 6/2004 | Obel et al. |
| 6,799,070 | B2 | 9/2004 | Wolfe et al. |
| 6,871,090 | B1 | 3/2005 | He et al. |
| 6,901,293 | B2 | 5/2005 | Rogers et al. |
| 2003/0007373 | A1 | 1/2003 | Satoh |

(Continued)

FOREIGN PATENT DOCUMENTS

| WO | WO 00/43065 | 7/2000 |
| WO | WO 2006/029007 A2 | 3/2006 |
| WO | WO 2008/036869 A1 | 3/2008 |

OTHER PUBLICATIONS

Patent Application entitled "Determination of Stimulation Output Capabilities Throughout Power Source Voltage Range," U.S. Appl. No. 11/943,858, filed Nov. 21, 2007, Torgerson.

(Continued)

*Primary Examiner*—George Manuel
*Assistant Examiner*—Robert N Wieland
(74) *Attorney, Agent, or Firm*—John W. Albrecht; Shumaker & Sieffert, P.A.

(57) ABSTRACT

Techniques for determining whether a medical device will be able to deliver stimulation according to a particular program throughout a useable voltage range of a power source of the medical device are described. According to some examples, the medical device charges a charge pump to a level sufficient to provide a stimulation output according to a stimulation program, determines a length of time that the charge pump charges at the present power source voltage level, and determines a time between stimulation pulses of the stimulation program. Whether the medical device will be able to deliver stimulation according to the program when the power source is at a power source voltage level lower than the present voltage level is determined based on the length of time the charge pump charges at the present voltage level of the power source and the time between stimulation pulses.

32 Claims, 8 Drawing Sheets

U.S. PATENT DOCUMENTS

| | | |
|---|---|---|
| 2003/0174078 A1 | 9/2003 | Ohlsson |
| 2003/0187485 A1 | 10/2003 | Sturman et al. |
| 2003/0204225 A1 | 10/2003 | Heathershaw et al. |
| 2004/0147983 A1* | 7/2004 | Czygan ............... 607/72 |
| 2004/0162592 A1 | 8/2004 | Betzold et al. |
| 2005/0180179 A1 | 8/2005 | Hirst |
| 2007/0135868 A1 | 6/2007 | Shi et al. |
| 2007/0156203 A1 | 7/2007 | Varrichio et al. |
| 2007/0191907 A1 | 8/2007 | Stein et al. |

OTHER PUBLICATIONS

Patent Application entitled "Determination of Stimulation Output Capabilities Throughout Power Source Voltage Range," U.S. Appl. No. 12/362,167, filed Jan. 29, 2009, Torgerson.

* cited by examiner

DETERMINATION OF STIMULATION OUTPUT CAPABILITIES THROUGHOUT POWER SOURCE VOLTAGE RANGE

This application claims the benefit of U.S. Provisional Application No. 61/110,453, filed Oct. 31, 2008, the entire content of which is incorporated herein by reference.

TECHNICAL FIELD

The invention relates to medical devices and, more particularly, to medical devices that include a power source and deliver electrical stimulation.

BACKGROUND

Medical devices may be used to treat a variety of medical conditions. Some medical devices are surgically implanted within the patient, while others are connected externally to the patient receiving treatment. Some medical devices receive electrical power from batteries, such as non-rechargeable primary cell batteries or rechargeable batteries, or another power source inside the medical device, such as a supercapacitor. An electrical stimulator is an example of a medical device that receives power from an internal source for delivery of a therapy to a patient.

Electrical stimulators may be used to deliver electrical stimulation therapy to patients to treat a variety of symptoms or conditions, such as chronic pain, tremor, Parkinson's disease, epilepsy, urinary or fecal incontinence, sexual dysfunction, obesity, or gastroparesis. An electrical stimulator may deliver stimulation therapy via leads that include electrodes located, as examples, proximate to the spinal cord, pelvic nerves, or stomach, on or within the brain, or within the pelvic floor. In general, the electrical stimulator delivers stimulation therapy in the form of electrical pulses or substantially continuous-time signals. The electrical stimulator may be external or implanted, for example, in a chest cavity, lower back, lower abdomen, or buttocks of a patient.

A clinician selects values for a number of programmable therapy parameters in order to define the stimulation therapy to be delivered to a patient. For example, the clinician may select an amplitude, which may be a current or voltage amplitude. When therapy is delivered in the form of electrical pulses, the clinician may also select a pulse width for a stimulation waveform to be delivered to the patient as well as a rate at which the pulses are to be delivered to the patient. The clinician may also select particular electrodes within an electrode set to be used to deliver the pulses or continuous-time signal, and the polarities of the selected electrodes. The selected electrodes and their polarities may be referred to as an electrode combination or configuration. A group of parameter values may be referred to as a program in the sense that they drive the electrical stimulation therapy to be delivered to the patient.

SUMMARY

In general, the disclosure is directed toward techniques for determining, for a given program, whether a medical device will be able to provide a stimulation output specified by the program throughout a voltage range of a power source of the medical device, e.g., throughout the life of a primary cell battery or between recharge cycles of a rechargeable power source, such as a rechargeable battery or supercapacitor. When the level of charge of a medical device power source depletes, the ability of the medical device to deliver adequate stimulation may be impacted. For example, decreased power source voltage may result in an out of regulation condition for a given program.

A medical device may utilize a charge pump to store charge acquired from a power source and deliver the stored charge as a stimulation output with stimulation parameter values, e.g., amplitude, pulse width, and/or pulse rate values, defined by a stimulation program. In examples in which the medical device delivers stimulation in the form of pulses, the charge pump may run to accumulate a charge sufficient to deliver a stimulation pulse, turn off once the charge level is reached, deliver the stimulation pulse, and run to accumulate a charge sufficient to deliver the next stimulation pulse. The length of time that the charge pump may run to accumulate the charge required to generate a stimulation pulse is limited by the time between pulses, or pulse rate, specified by the stimulation program.

As the voltage level of the power source decreases, the rate at which the charge pump may accumulate charge from the power source, i.e., charge per time, also decreases. Therefore, as the power source voltage level decreases, the charge pump may need to run for a longer amount of time to accumulate the same amount of charge, e.g., the charge required to deliver a stimulation output specified by a stimulation program. If the charge pump is unable to accumulate the charge required to generate the stimulation output in between pulses, an out of regulation condition may occur.

In one example, the disclosure provides a method comprising determining a length of time a charge pump charged at a present voltage level of a power source to reach a level of charge on the charge pump sufficient to provide a stimulation output according to a stimulation program, determining a total time interval available for the charge pump to charge during delivery of stimulation according to the stimulation program, and determining whether the medical device will be able to deliver stimulation according to the program at a voltage level of the power source that is lower than the present voltage level of the power source based on the length of time the charge pump charged at the present voltage level of the power source and the total time interval available for the charge pump to charge.

In another example, the disclosure provides medical device system comprising a medical device and a processor. The medical device comprises a power source at a present power source voltage level, and a signal generator that generates electrical stimulation, wherein the signal generator comprises a charge pump coupled to the power source. The processor determines a length of time that the charge pump charged at the present power source voltage level to reach a level of charge on the charge pump sufficient to provide a stimulation output according to a stimulation program, determines a total time interval available for the charge pump to charge during delivery of stimulation according to the stimulation program, and determines whether the medical device will be able to deliver stimulation according to the program at a voltage level of the power source that is lower than the present voltage level of the power source based on the length of time the charge pump charged at the present voltage level of the power source and the total time interval available for the charge pump to charge.

In another example, the disclosure provides a medical device system comprising means for determining a length of time a charge pump charged at a present voltage level of a power source to reach a level of charge on the charge pump sufficient to provide a stimulation output according to a stimulation program, means for determining a total time interval available for the charge pump to charge during delivery of stimulation according to the stimulation program, and means for determining whether the medical device will be able to deliver stimulation according to the program at a power source voltage level lower than a present voltage level of a power source based on the length of time the charge pump charges at the present voltage level of the power source and the time between stimulation pulses.

In other examples, the disclosure provides a computer-readable medium or computer-readable media comprising instructions that cause a programmable processor to perform any of the methods described herein.

The details of one or more examples are set forth in the accompanying drawings and the description below. Other features, objects, and advantages will be apparent from the description and drawings, and from the claims.

DETAILED DESCRIPTION

Figure 1:
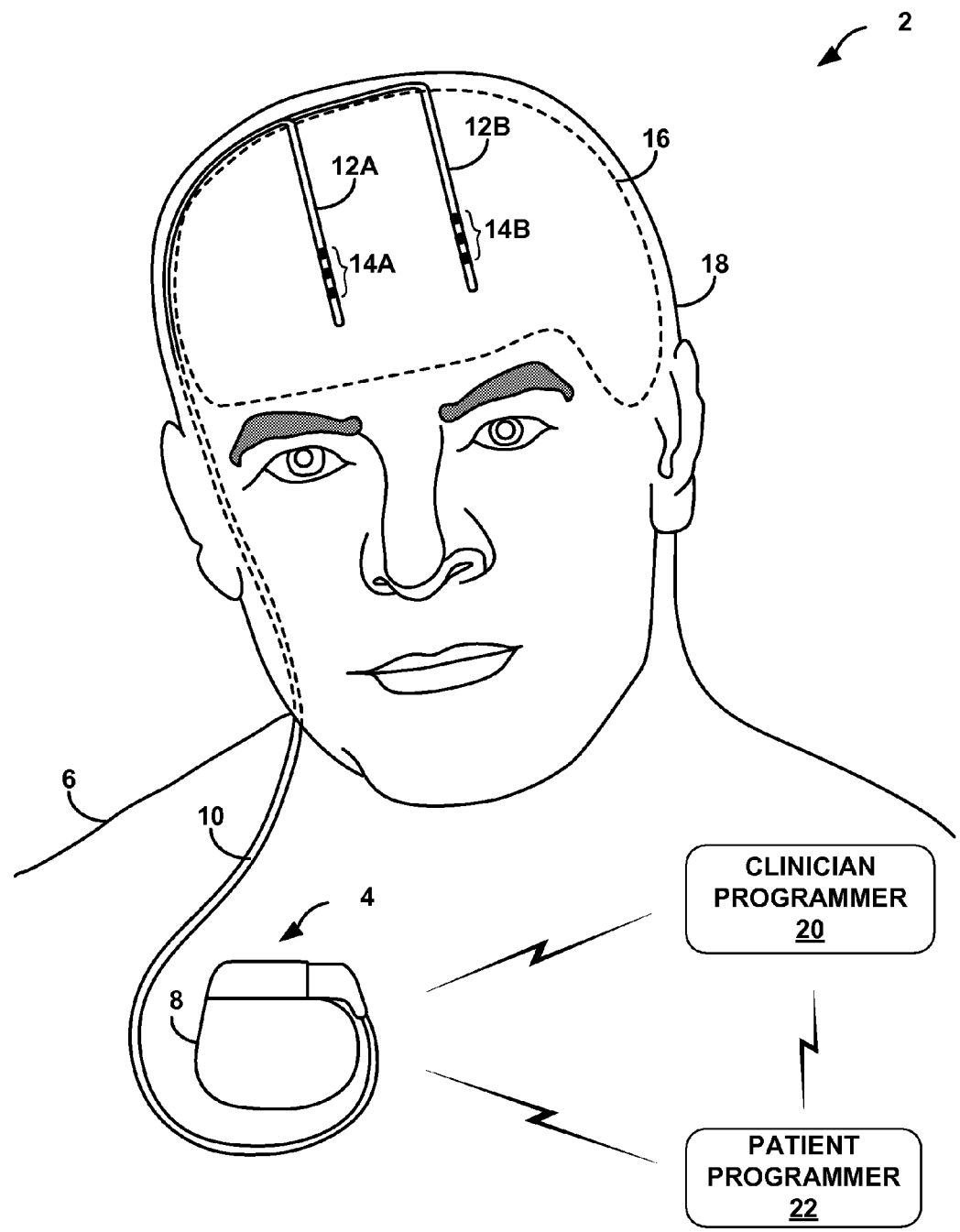
FIG. 1 is a schematic perspective view of an example therapy system, which includes an electrical stimulator coupled to a stimulation lead.

FIG. 1 is a schematic perspective view of an example therapy system 2, which includes an example medical device 4. In the example of FIG. 1, medical device 4 has been implanted in patient 6. For example, medical device 4 may be subcutaneously implanted in the body of patient 6, e.g., in a chest cavity, lower back, lower abdomen, buttocks, or cranium of patient 6. In other examples, a medical device may be external external. Patient 6 will ordinarily, but not necessarily, be a human patient.

In the example illustrated in FIG. 1, medical device 4 is an electrical stimulator and provides a programmable stimulation signal, e.g., in the form of electrical pulses or substantially continuous-time signals, that is delivered to patient 6 by implantable medical lead 10 and, more particularly, via one or more stimulation electrodes carried by lead 10. Medical device 4 may also be referred to as a pulse or signal generator. In the example of FIG. 1, the distal end of lead 10 is bifurcated and includes two segments 12A and 12B. Segments 12A and 12B each include an electrode array 14A and 14B, respectively. At least some of the electrodes of arrays 14A and 14B may be stimulation electrodes to deliver a stimulation signal from medical device 4 to patient 6. In some examples, lead 10 may also carry one or more sense electrodes to permit electrical medical device 4 to sense electrical signals from patient 6. In various examples, medical device 4 may be coupled to one or more leads, which may or may not be bifurcated.

A proximal end of lead 10 may be both electrically and mechanically coupled to medical device 4 either directly or indirectly, e.g., via a lead extension. In particular, conductors disposed in the lead body may electrically connect stimulation electrodes adjacent to the distal end of lead 10, e.g., the electrodes of electrode arrays 14A and 14B, to medical device 4.

In the example shown in FIG. 1, lead 10 extends to brain 16 of patient 6, e.g., through cranium 18 of patient 6. Medical device 4 may deliver deep brain stimulation (DBS) or cortical stimulation (CS) therapy, as examples, to patient 6 via the electrodes of arrays 14A and 14B of lead 10 to treat any of a variety of movement disorders, including tremor, Parkinson's disease, spasticity, epilepsy, or dystonia.

Therapy system 2 may be useful in other stimulation applications, including pelvic floor stimulation, spinal cord stimulation, cortical surface stimulation, neuronal ganglion stimulation, gastric stimulation, peripheral nerve stimulation, or subcutaneous stimulation. Such therapy applications may be targeted to a variety of disorders such as chronic pain, peripheral vascular disease, angina, headache, tremor, depression, Parkinson's disease, epilepsy, urinary or fecal incontinence, sexual dysfunction, obesity, or gastroparesis. Further, therapy system 2 may be useful in non-neurostimulation contexts. For example, medical device 4 may be used to deliver stimulation to a target muscle or myocardial tissue site via leads to, for example, provide functional electrical stimulation or cardiac stimulation, e.g., cardiac pacing. In various examples, therapy system 2 may deliver therapy to any nerve or other tissue site in patient 6.

Therapy system 2 also may include a clinician programmer 20 and a patient programmer 22, as illustrated in FIG. 1. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry, e.g., radio frequency telemetry, with medical device 4 to download programs and, optionally, upload operational or physiological data stored by medical device 4. In this manner, the clinician may periodically interrogate medical device 4 to evaluate efficacy and, if necessary, modify the programs or create new programs. In some examples, clinician programmer 20 transmits programs to patient programmer 22 in addition to or instead of medical device 4.

Like clinician programmer 20, patient programmer 22 may be a handheld computing device. Patient programmer 22 may also include a display and input keys to allow patient 6 to interact with patient programmer 22 and medical device 4. In this manner, patient programmer 22 provides patient 6 with a user interface for control of the stimulation therapy delivered by medical device 4. For example, patient 6 may use patient programmer 22 to start, stop or adjust electrical stimulation therapy. In particular, patient programmer 22 may permit patient 6 to adjust stimulation parameters of a program such as duration, current or voltage amplitude, pulse width and pulse rate. Patient 6 may also select a program, e.g., from among a plurality of stored programs, as the current program to control delivery of stimulation by medical device 4.

In some examples, medical device 4 delivers stimulation according to a group of programs at any given time. Each program of such a program group may include respective values for each of a plurality of therapy parameters, such as respective values for each of amplitude (e.g., current or voltage amplitude), pulse width, pulse rate and electrode combination. Medical device 4 may interleave pulses or other signals according to the different programs of a program group, e.g., cycle through the programs, to, for example, simultaneously treat different symptoms or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by medical device 4.

Medical device 4, clinician programmer 20, and patient programmer 22 may communicate via cables or a wireless communication, as shown in FIG. 1. Clinician programmer 20 and patient programmer 22 may, for example, communicate via wireless communication with medical device 4 using RF telemetry techniques known in the art. Clinician programmer 20 and patient programmer 22 also may communicate with each other using any of a variety of local wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with medical device 4.

Figure 2:
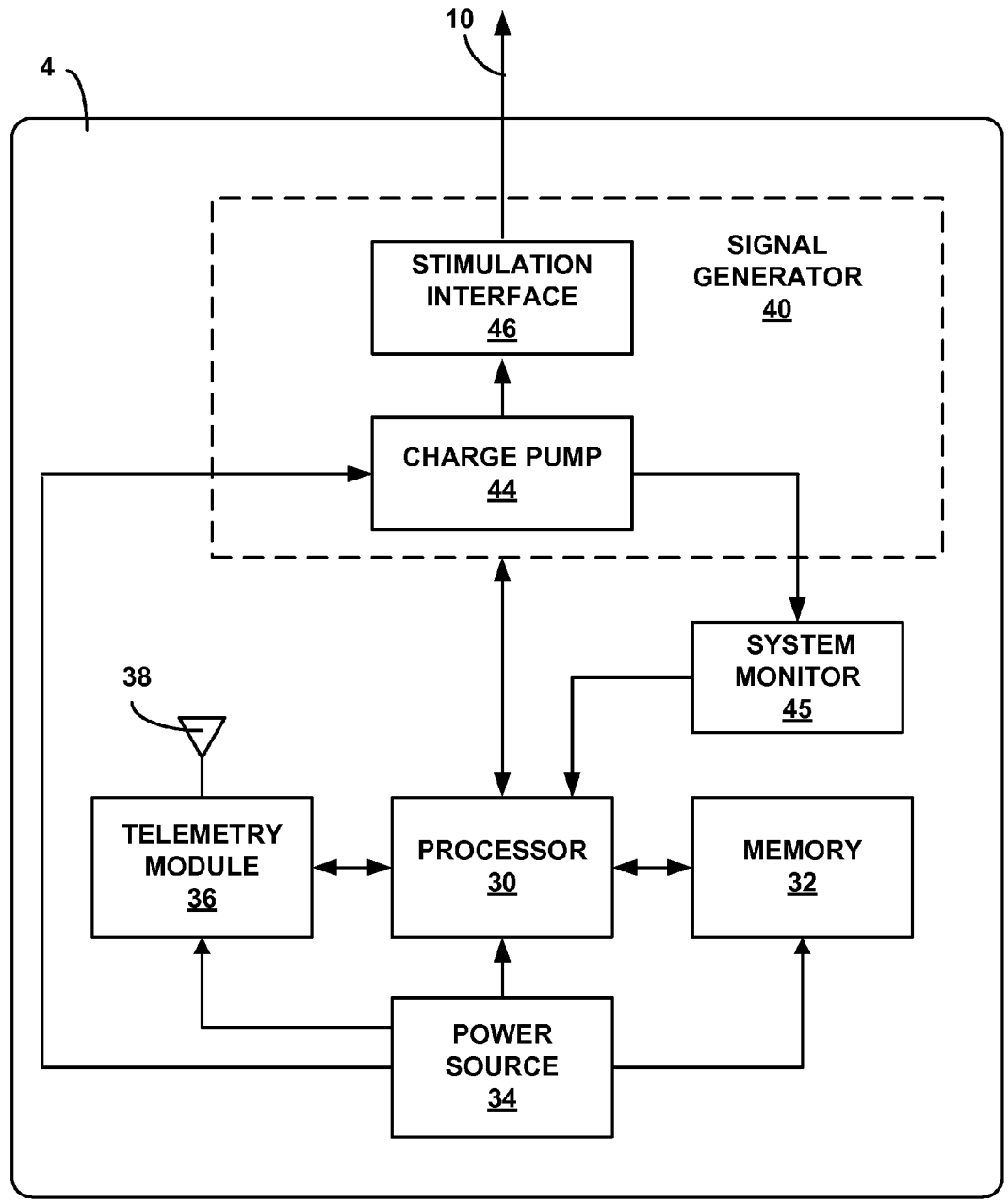
FIG. 2 is a functional block diagram illustrating various components of an example electrical stimulator.

FIG. 2 is a functional block diagram illustrating various components of medical device 4 according to one example. In the example of FIG. 2, medical device 4 includes processor 30, memory 32, power source 34, telemetry module 36, antenna 38, and signal generator 40. Telemetry module 36 may permit communication with clinician programmer 20 and patient programmer 22 to receive, for example, new programs or program groups, or adjustments to programs or program groups.

Processor 30 may include one or more microprocessors, digital signal processors (DSPs), application-specific integrated circuits (ASICs), field-programmable gate arrays (FPGAs), or other digital logic circuitry. Processor 30 controls operation of medical device 4, e.g., controls signal generator 40 to deliver stimulation therapy according to a selected program or group. For example, processor 30 may control signal generator 40 to deliver electrical signals with current or voltage amplitudes, pulse widths (if applicable), and rates specified by one or more stimulation programs. Processor 30 may also control signal generator 40 to deliver the stimulation signals via subsets of the electrodes of arrays 14A and 14B with polarities, the subsets and polarities specified as electrode combinations or configurations by one or more programs.

At any given time, processor 30 may control signal generator 40 to deliver stimulation according to a selected one or more of a plurality of programs or program groups stored in memory 32. Memory 32 may include any magnetic, electronic, or optical media, such as random access memory (RAM), read-only memory (ROM), electronically-erasable programmable ROM (EEPROM), flash memory, or the like. Memory 32 may store program instructions that, when executed by processor 30, cause the processor to perform the functions ascribed to it and medical device 4 herein.

Telemetry module 36 may include a transceiver to permit bi-directional communication between medical device 4 and each of clinician programmer 20 and patient programmer 22. Telemetry module 36 may include an antenna 38 that may take on a variety of forms. For example, antenna 38 may be formed by a conductive coil or wire embedded in a housing associated with medical device 4. Alternatively, antenna 38 may be mounted on a circuit board carrying other components of electrical stimulator 4 or take the form of a circuit trace on the circuit board.

Power source 34 may be a non-rechargeable primary cell battery or a rechargeable battery and may be coupled to power circuitry. However, the invention is not limited to examples in which the power source is a battery. In another example, as an example, power source 34 may comprise a supercapacitor. In some examples, power source 34 may be rechargeable via induction or ultrasonic energy transmission, and include an appropriate circuit for recovering transcutaneously received energy. For example, power source 34 may be coupled to a secondary coil and a rectifier circuit for inductive energy transfer.

Signal generator 40 produces an electrical stimulation signal in accordance with a program based on control signals from processor 30. Signal generator 40 may include a DC to DC converter and a stimulation interface 46. In the example illustrated in FIG. 2, the DC to DC converter is a charge pump 44, e.g., an inductor-based and/or capacitor-based charge pump.

Charge pump 44 selectively, e.g., utilizing switches and based on signals from processor 30, applies energy from power source 34 to storage elements, e.g., capacitors or inductors, to build up charge on the charge pump for delivery of a stimulation signal, e.g., pulse. When pulses are delivered, processor 30 may control the pulse rate by controlling charge pump 44 to discharge at specified time intervals. For example, under the control of processor 30, charge pump 44 may accumulate energy from power source 34. Once charge pump 44 builds up enough charge to generate the stimulation output according to the program selected for therapy delivery, processor 30 may control charge pump 44 to stop accumulating charge. Processor 30 may control charge pump 44 to discharge for delivery of a pulse at a specified time based on the pulse rate of the selected therapy program.

When charge pump 44 discharges, charge pump 44 transfers charge to stimulation interface 46 and the amount of charge stored on charge pump 44 decreases. Therefore, after charge pump 44 discharges for delivery of a stimulation pulse, processor 30 may control charge pump 44 to accumulate energy from power source 34 to recharge charge pump 44 to the level required by the selected stimulation program. The amount of charge stored on charge pump 44 is dependent on the length of time that charge pump 44 runs and the voltage level of power source 34 when charging occurs. Charge pump 44 may stop charging after charge pump 44 accumulates enough charge for generation of the stimulation output according to the selected program. Processor 30 may control charge pump 44 to discharge for delivery of additional pulses at time intervals consistent with the pulse rate of the selected program, and charge pump 44 may recharge between pulses.

Stimulation interface 46 conditions charge from charge pump 44 to produce an electrical stimulation signal, e.g., a pulse, under control of processor 30 for application to at least some electrodes of electrode arrays 14A and 14B carried by lead 10. Stimulation interface 46 may control the voltage or current amplitude of the signal based on signals from processor 30. Stimulation interface 46 may also control to which electrodes of arrays 14A and 14B the stimulation signal is provided, and the polarities of the electrodes, based on signals from processor 30.

Figure 3:
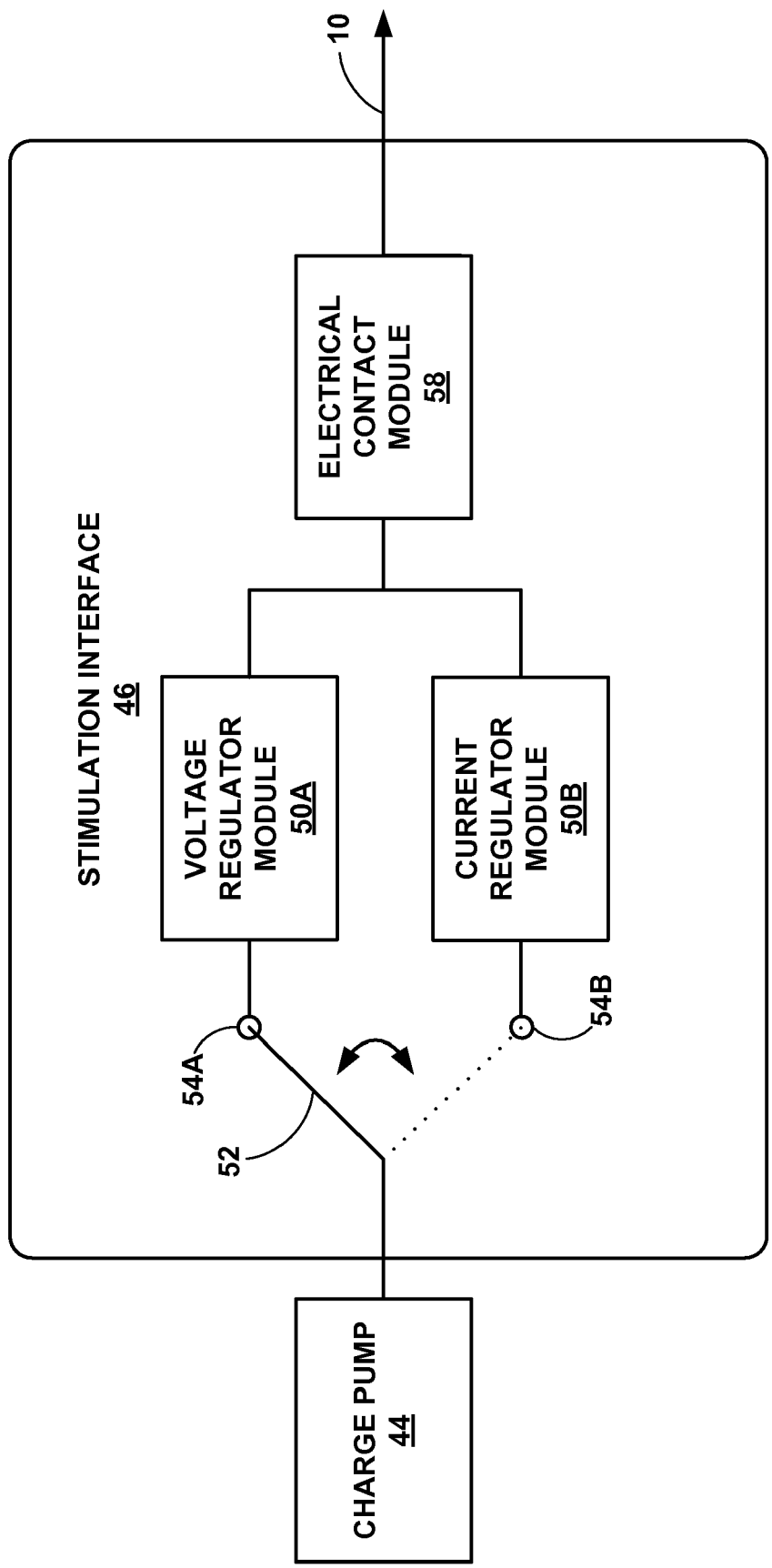
FIG. 3 is a block diagram illustrating various components of an example stimulation interface.

FIG. 3 is a block diagram illustrating various components of stimulation interface 46 according to one example. In the example illustrated in FIG. 3, stimulation interface 46 includes voltage regulator module 50A, current regulator module 50B, and electrical contact module 58. Voltage regulator module 50A may include, for example, a voltage regulator that outputs a substantially constant voltage at a programmable value, and current regulator module 50B may include, for example, a current regulator that outputs a substantially constant current at a programmable value.

In the illustrated example, stimulation interface 46 is selectively, e.g., based on a signal from processor 30, able to deliver either constant voltage or constant current stimulation pulses to patient 6 using voltage regulator module 50A or current regulator module 50B, respectively. However, the invention is not limited to examples in which both constant voltage and constant current pulses are available. Other examples may provide only constant voltage pulses, or only constant current pulses. In some examples, medical device 4 may deliver constant voltage pulses without a voltage regulator module 50A. Instead, processor 30 may control the charge pump 44 to store the voltage required by the selected stimulation program, and charge pump 44 may transfer the required voltage to electrical contact module 58. Charge pump 44 may regulate how much voltage is outputted to the electrodes of lead 10 via electrical contact module 58. Furthermore, as indicated above, the invention is not limited to examples in which stimulation is in the form of pulses.

In the example illustrated by FIG. 3, when therapy is delivered to patient 6 using constant voltage mode, processor 30 may actuate switch 52 to connect the output of charge pump 44 to node 54A, which connects to voltage regulator module 50A. In this manner, the output of voltage regulator module 50A, a constant voltage at the amplitude specified by a stimulation program, is output to lead 10 via electrical contact module 58.

When stimulation is delivered to patient 6 using constant current mode, charge pump 44 is coupled to current regulator module 50B via switch 52 as controlled by processor 30. When constant current stimulation is delivered to patient 6, processor 30 may actuate switch 52 to connect the output of charge pump 44 to node 54B of current regulator module 50B. Current regulator module 50B will output a constant current to lead 10 via electrical contact module 58, at an amplitude specified by a stimulation program. In this manner, one of regulator modules 50A and 50B (collectively "regulator modules 50") may be active (referred to as the "active regulator module 50"), e.g., connected to charge pump 44, depending on whether medical device 4 is delivering constant voltage or constant current stimulation.

The voltage that charge pump 44 inputs into the active regulator module 50 may be higher than the output voltage outputted by the active regulator module 50. The voltage drop across the active regulator module 50 may provide adequate "headroom" for the active regulator module 50 to maintain the desired output value. For example, each of regulator modules 50 may require a minimum voltage drop between its input and output to ensure proper operation. The minimum voltage drop may be referred to as the required headroom.

Electrical contact module 58 may include a plurality of switches that may be controlled by processor 30. Each of the switches within electrical contact module 58 may be coupled to a conductor within lead 10 to allow processor 30 to control therapy delivery to a selected subset of electrodes according to an electrode configuration specified by a current stimulation program. However, the invention is not limited to examples that include an electrical contact module comprising a plurality of switches to selectively multiplex the output of an active regulator module 50 across a plurality of electrodes. In other examples, each electrode of a lead 10 may be associated with a respective voltage and/or current source, e.g., voltage regulator module 50A and/or current regulator module 50B. Accordingly, in some examples, selection of electrodes and polarities by processor 30 according to an electrode configuration specified in a stimulation program may involve selection of a voltage or current source by the processor, instead of or in addition to switching the source across selected electrodes.

The active regulator module 50 may receive an input signal from charge pump 44. As described with respect to FIG. 2, processor 30 may control the amount of charge stored on charge pump 44. For example, processor 30 may control charging circuit 42 to charge the charge pump 44 to the minimum level necessary to produce the stimulation output specified by the selected program. In this manner, charge pump 44 may provide the active regulator module 50 with the minimum input that the active regulator module 50 requires to produce the stimulation output. The minimum input required by the active regulator module 50 may correspond to the sum of the stimulation output and the required headroom of the active regulator module 50.

Referring again to FIG. 2, IMD, medical device 4 may include a system monitor 45. System monitor 45 may by used to detect whether medical device 4 is able to deliver stimulation according to a presently selected stimulation program at a lower power source voltage level. In the example illustrated in FIG. 2, system monitor 45 is coupled to charge pump 44. As described in greater detail below, system monitor 45 may monitor the voltage on charge pump 44 to determine whether medical device 4 is able to deliver stimulation according to the present program at the lower power source voltage level based on a duty cycle of charge pump 44.

In some examples, system monitor 45 may monitor any of a variety of voltages or other electrical parameter values within signal generator 40, in addition to the voltage on charge pump 44, and provide such values to processor 30. Processor may determine whether medical device 4 is able to deliver stimulation according to a presently selected stimulation program at a lower power source voltage level, and otherwise monitor the condition or performance of signal generator 40, based on such values. In some examples, system monitor 45 may be implemented as a functional component provided by processor 30.

If processor 30 determines that medical device 4 is, or will be, unable to deliver stimulation according to the selected program based on a parameter measured by system monitor 45, processor 30 may report the determination over a telemetry channel via telemetry module 36. In response to such a report, a user may wish to modify the stimulation program, e.g., decrease an amplitude and/or pulse rate of the stimulation signal. In examples in which power source 34 is rechargeable, a user may wish to recharge power source 34 in response to such a report. The report may be provided to the user, e.g., clinician or patient, via one of programmers 20, 22, or another external device. In addition to an indication that the medical device is, or will be, unable to deliver therapy according to the program, the external device may also provide recommendations to the user about how to respond, e.g., decrease an intensity of stimulation, recharge the power source, or the like.

Figure 4:
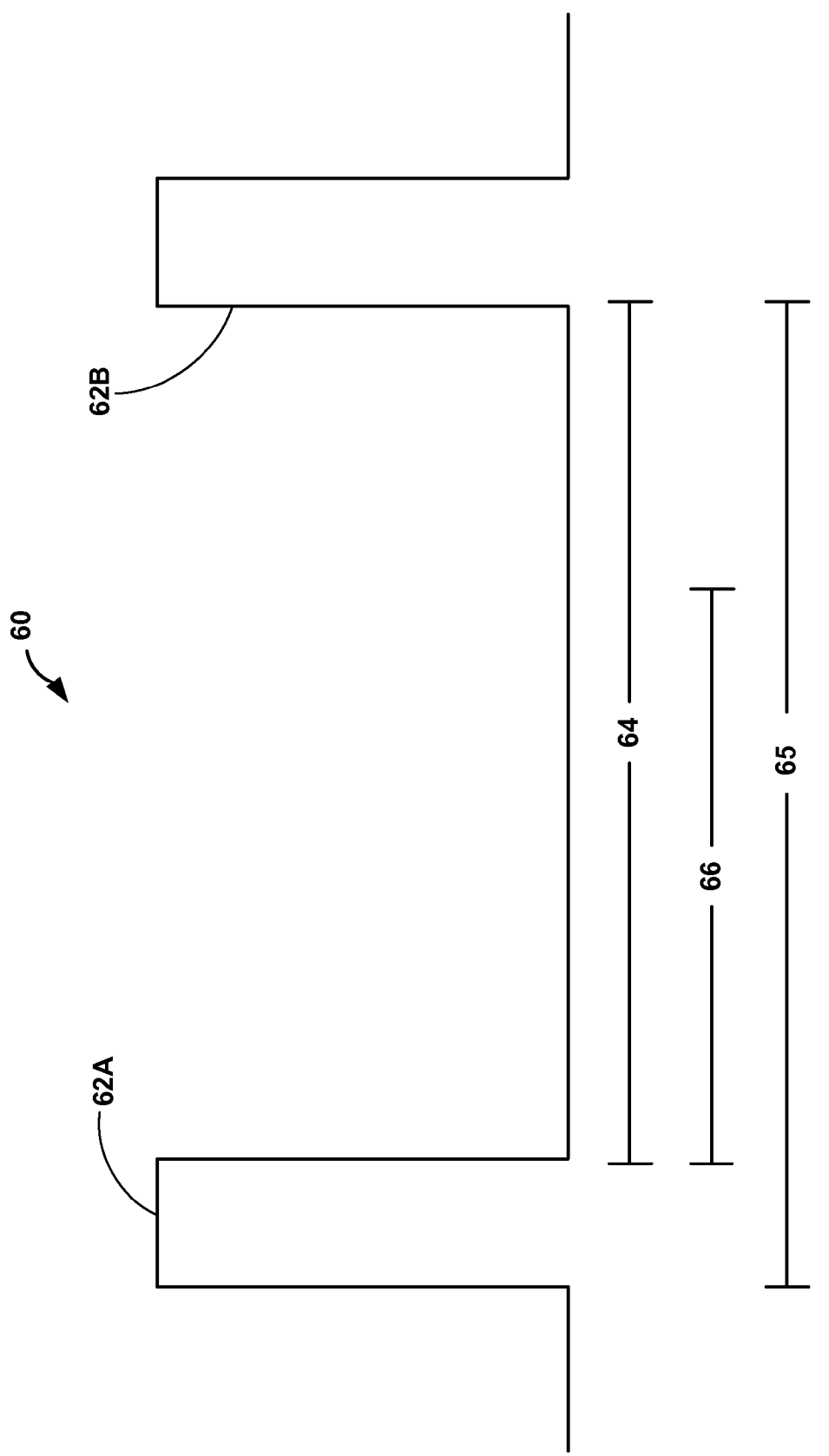
FIG. 4 is a timing diagram of an example waveform including two consecutive stimulation pulses separated by a time interval.

FIG. 4 illustrates an example waveform 60 including two consecutive stimulation pulses 62A and 62B (collectively "stimulation pulses 62") separated by time interval 64. As described with respect to FIG. 2, charge pump 44 discharges to deliver pulses 62 and recharges between pulses 62, i.e., during time interval 64. To aid in maximizing the life of power source 34 (FIG. 2), charge pump 44 may stop charging after charge pump 44 has accumulated the minimum voltage required to produce the next stimulation pulse. Therefore, charge pump 44 may only run, i.e., charge, for a portion of time interval 64.

The rate at which charge pump 44 accumulates charge and, consequentially, the length of time that charge pump 44 is charged prior to achieving a desired charge level, both depend on the voltage level of power source 34. For example, as the voltage level of power source 34 decreases, charge pump 44 would need to charge longer to produce the same stimulation pulse. Processor 30 may determine whether medical device 4 will be able to support the selected therapy program throughout the useable life of power source 34 based on this principle. For example, processor 30 may predict how long charge pump 44 would need to be charged to accumulate the charge required to generate the stimulation output of the selected program as power source 34 reaches depletion and compare the required run time of charge pump 44 to the allowed time interval 64 between pulses 62.

In one example, processor 30 may determine whether medical device 4 will be able to support the selected therapy program throughout the useable life of power source 34 based on the duty cycle of charge pump 44. Processor 30 may determine the duty cycle of charge pump 44 by comparing the amount of time that charge pump 44 is charged to the available time 64 that charge pump 44 could be charged between pulses 62. For example, duty cycle may refer to the fraction of time interval 64 that charge pump 44 is charged. Processor 30 may set a duty cycle threshold 66 to account for a future drop in the voltage level of power source 34. For example, processor 30 may set duty cycle threshold 66 to seventy percent of time interval 64 when power source 34 is fully charged, and eighty five percent of time interval 64 when power source 34 is half charged. Processor 30 may determine duty cycle threshold 66 based on a function or look-up table, e.g., stored in memory 32, that relates the percentage or fraction or other measurement of the degree of charge of power source 34 to a percentage, fraction or the like of time interval 64. In some examples, look-up table or function may be based from or include the association of a duty cycle threshold 66 equal to one hundred percent of interval 64 when power source 34 reaches depletion.

The value of duty cycle threshold 66 may be determined, e.g., by processor 30, based on the present voltage level of power source 34, since the future drop in the voltage level of power source 34 changes with the present voltage level of power source 34. If power source 34 is fully charged, the expected change in voltage level of power source 34 may be at a maximum and, consequentially, the expected increase in the charge time of charge pump 44 as power source 34 reaches depletion will also be at a maximum. If power source 34 is less than fully charged, the expected decrease in the voltage level of power source 34 may be less than a maximum and, consequentially, the expected increase in the run time of charge pump 44 as power source 34 reaches depletion will also be less than a maximum. Therefore, the value of duty cycle threshold 66 may increase as the voltage level of power source 34 decreases. As described in further detail with respect to FIG. 5, if the duty cycle of charge pump 44 at the present voltage level of power source 34 is greater than duty cycle threshold 66, processor 30 may determine that medical device 4 will not be able to support the selected therapy program throughout the useable life of power source 34.

Although threshold 66 is described primarily as a percentage or fraction of the available time between pulses, other types of thresholds are also contemplated. For example, processor 30 may subtract a specified value from time interval 64 to yield threshold 66. However, since time interval 64 between pulses 62 may vary between stimulation programs, a threshold determined as a percentage of the available time between pulses may be particularly useful. Since the duty cycle threshold may represent the fraction of time interval 66 the charge pump 44 is charged, a single value for the present voltage level of power source 34 may be more easily applied to any stimulation program.

In some examples, charge pump 44 may continue to accumulate charge as it discharges to deliver pulses 62. In this manner, charge pump 44 may run substantially continuously. The active regulator module 50 may smooth out fluctuations in the voltage supplied by charge pump 44 that may occur when charge pump 44 runs to accumulate charge and discharges to deliver pulses 62 simultaneously. In examples in which charge pump 44 runs substantially continuously, charge pump 44 may charge while pulses 62 are delivered in addition to during time interval 64 between pulses 62. For example, to deliver pulse 62B, charge pump 44 may charge during the time 67 that pulse 62A is delivered, e.g., during the duration of pulse 62A, and during time interval 64 between pulses 62A and 62B.

Processor 30 may determine a time interval 64 between stimulation pulses 62 of a stimulation program and the pulse duration 67 of a stimulation pulse to determine the total time interval 65 that charge pump 44 may run to accumulate charge to deliver a pulse 62. In embodiments in which charge pump 44 may charge substantially continuously, processor 30 may use time interval 65, which includes the time interval between pulses 64 and the pulse duration 67, rather than time interval 64 to determine whether medical device 4 will be able to deliver stimulation according to a program at a voltage level of power source 34 that is lower than the present voltage level of power source 34.

Figure 5:
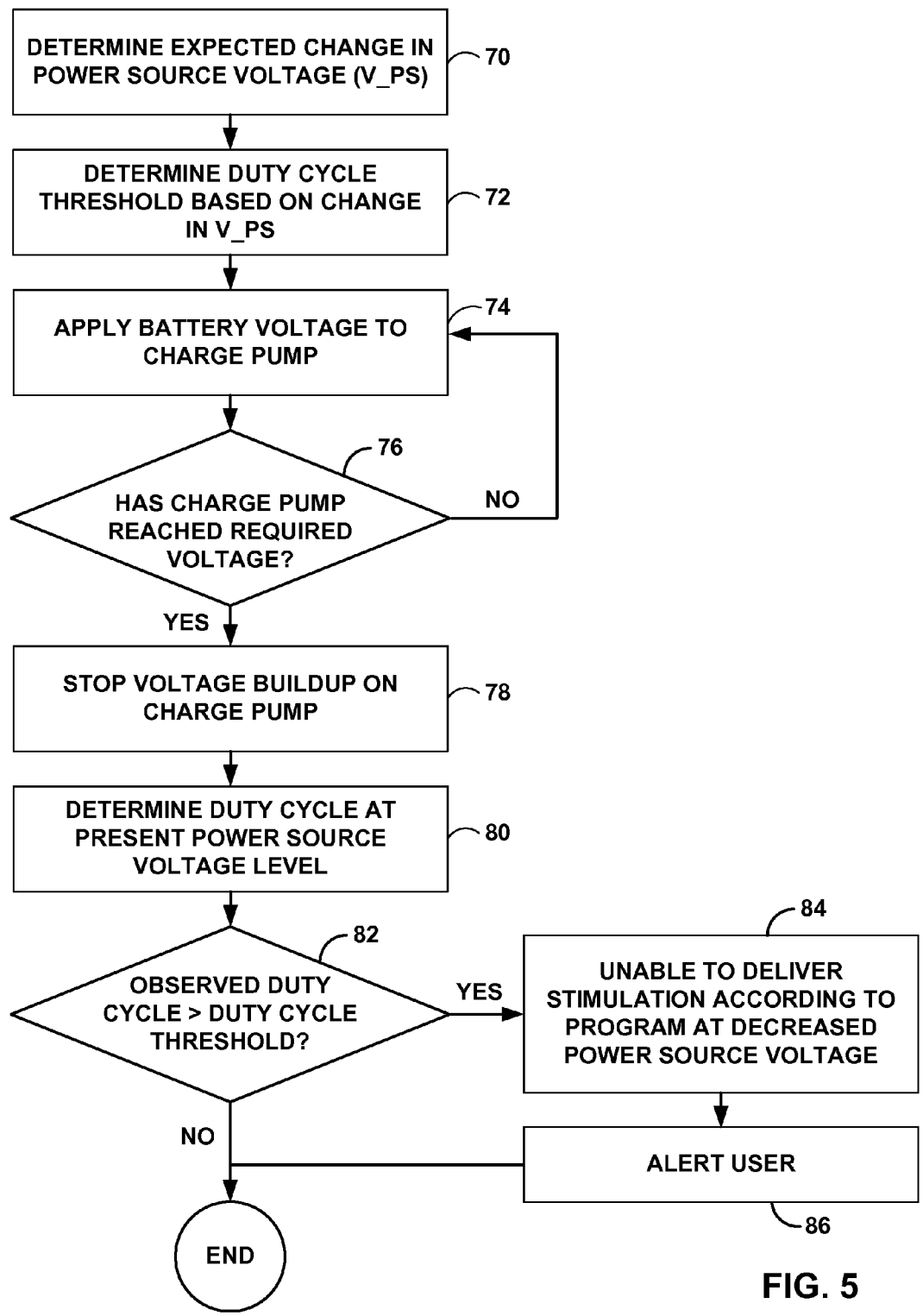
FIG. 5 is a flow diagram illustrating an example method of determining whether a medical device will be able to deliver stimulation according to a program at a lower battery voltage level.

FIG. 5 is a flow diagram illustrating one example method of determining whether medical device 4 will be able to support the selected therapy program throughout the useable life of power source 34. The method of FIG. 5 is described as being performed by processor 30 of medical device 4. However, in other examples, one or more aspects of the method may additionally or alternatively be performed by a processor or other component of one or both of programmers 20, 22, or a local or remote computing device or server in communication with medical device 4 and/or one or both of programmers 20, 22.

According to the illustrated example, processor 30 may determine the expected change in voltage level of power source 34 as power source 34 depletes from its present voltage level to a lower voltage level (70). For example, processor 30 may control system monitor 45 to measure the present voltage level of power source 34. Additionally, memory 32 may store a value of the lower voltage level of power source 34. The lower voltage level of power source 34 may be the voltage level of power source 34 just prior to full depletion. For example, the lower voltage level of power source 34 may be a threshold voltage that defines a minimum voltage level of power source 34 below which therapy delivery by medical device 4 will cease. Processor 30 may calculate the difference between the present voltage level of power source 34 and the lower voltage level of power source 34. This difference in voltage levels may represent the expected change in the voltage level of power source 34 as power source 34 depletes from the present voltage level to the lower voltage level.

Processor 30 may also determine a duty cycle threshold based on the expected change in the voltage level of power source 34 (72). As previously described, the value of the duty cycle threshold may account for a future drop in the voltage level of power source 34. For example, as the expected change in the voltage level of power source 34 increases, the expected change in the run time of charge pump 44 may increase and, consequentially, the value of the duty cycle threshold may decrease.

Charge pump 44 may, under control of processor 30, accumulate energy from power source 34 for delivery of a stimulation signal, e.g., pulse (74). Processor 30 may monitor the voltage on charge pump 44 via system monitor 45. Once processor 30 determines that charge pump 44 has built up enough charge to generate the stimulation output according to the program selected for therapy delivery (76), processor 30 may stop the charging by charge pump 44 (78). The amount of charge stored on charge pump 44 is dependent on the length of time that charge pump 44 runs and the voltage level of power source 34 when charging occurs. Charge pump 44 may stop charging after building up enough charge to generate the stimulation output according to the selected program (78). As the voltage level of power source 34 decreases, charge pump 44 may need to run longer to build up the same amount of charge on the charge pump.

Processor 30 may determine the duty cycle of charge pump 44 at the present voltage level of power source 34 based on how long charge pump 44 ran in order to reach the desired voltage level (80). For example, processor 30 may maintain a timer that measures how long charge pump 44 runs in order to reach the desired voltage level. Processor 30 may also determine the time interval 64 between consecutive pulses 62 based on the pulse rate specified by the selected program. After charge pumps stops running, processor 30 may calculate the ratio of the length of time that charge pump 44 ran to the time interval 64 between consecutive pulses 62 to determine the duty cycle of charge pump 44 at the present voltage level of power source 34.

Processor 30 may compare the duty cycle observed at the present voltage level of power source 34 to the duty cycle threshold (82). If the observed duty cycle is greater than the duty cycle threshold, processor 30 may determine that medical device 4 will be unable to deliver stimulation according to the selected stimulation program at the lower voltage level of power source 34 (84).

In response the determination that medical device 4 will not be able to correctly deliver the stimulation specified by the selected program at the lower battery voltage level, processor 30 may control telemetry module 36 to deliver an alert to a user, e.g., by controlling telemetry module 36 to transmit an indication or information to one or both of programming devices 20, 22, in the manner discussed above (86). As discussed above, a programming device may also provide recommendations to the user about how to avoid ineffective stimulation as power source 34 depletes, e.g., by suggesting a decrease in the intensity of stimulation, recharging power source 34 before its charge level reaches a specified lower power source voltage level, replacing power source 34 or medical device 4 when its voltage depletes to a certain value, or the like. As one example, processor 30 may suggest a decreased pulse rate such that the charging time required by charge pump 44 at the lower voltage level of power source 34 is less than the time between stimulation pulses.

In some examples, processor 30 may reconfigure a minimum voltage level of power source 34 based on the determination that the medical device will be unable to deliver therapy according to the selected program at the lower battery voltage level. For example, processor 30 may inform a user of a programming device, e.g., programming device 20 or 22, or another external device that the medical device will be unable to deliver therapy according to the selected program at a lower battery voltage level via telemetry module 36. In addition to the indication that the medical device will be unable to deliver therapy according to the selected program at the lower power source voltage level, the external device may provide recommendations to the user about how to respond, e.g., decrease an intensity of stimulation, recharge the power source more frequently, or the like. In addition to or instead of such recommendations, the external device may suggest reconfiguring the minimum voltage level of power source 34, such that power source 34 is replaced or recharged prior to reaching the lower power source voltage level.

Processor 30 may suggest a new minimum voltage level of power source 34 based on the duty cycle of charge pump 44 at the present voltage level of power source 34. For example, processor 30 may calculate a maximum allowable change in voltage level of power source 34, e.g., percent change or absolute change, given the duty cycle of charge pump 44 at the present voltage level to determine the new minimum voltage level of power source 34. The new minimum voltage level of power source 34 may correspond to a voltage level in which the duty cycle of charge pump 44 approaches one hundred percent, i.e., the required charge time of charge pump 44 approaches the time interval 64 between pulses 62. As described in further detail with respect to FIG. 8, in examples in which power source 34 is rechargeable, the external device may display a recharge frequency necessary to prevent the selected program from falling out of regulation.

Figure 6:
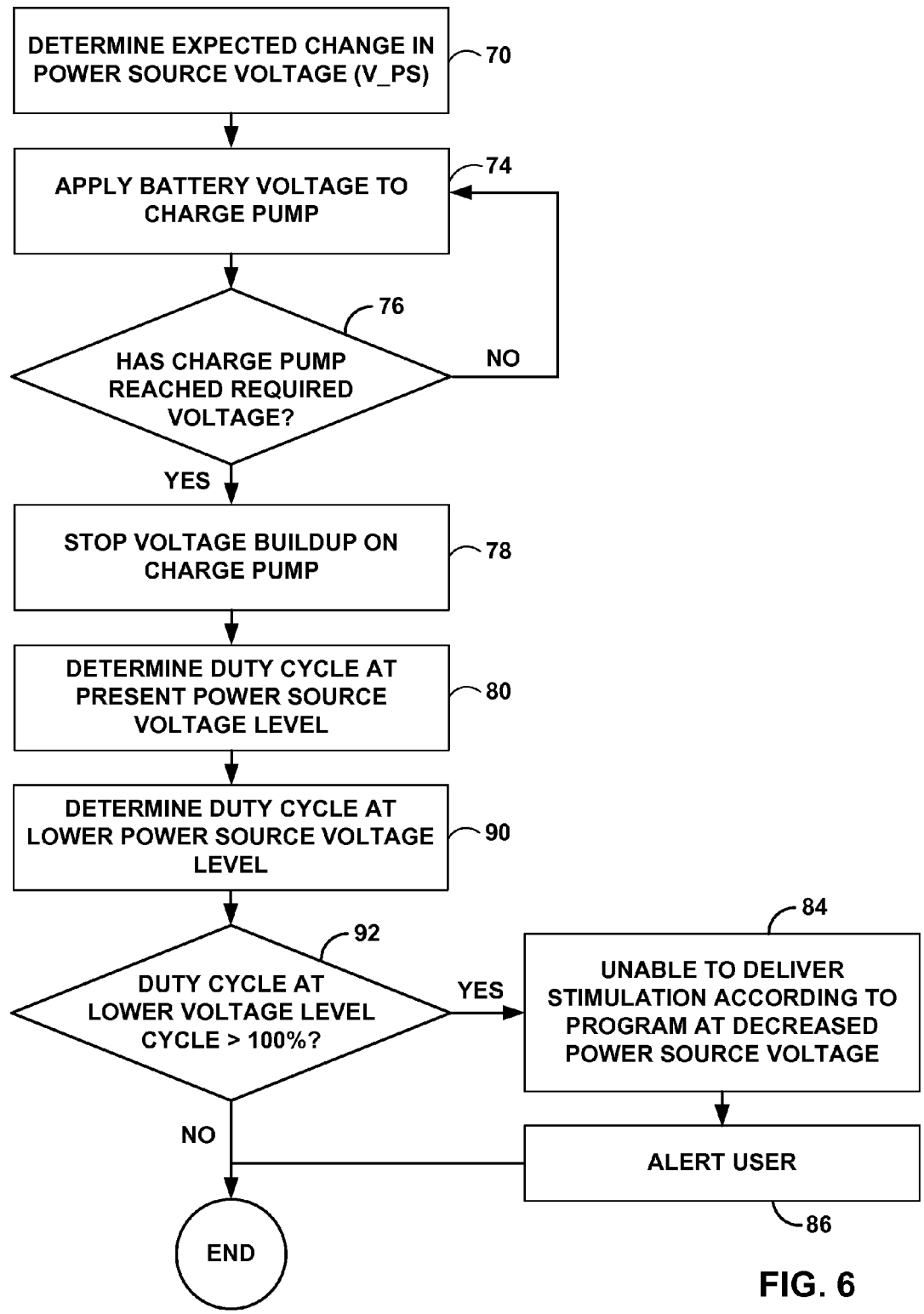
FIG. 6 is a flow diagram illustrating another example method of determining whether a medical device will be able to deliver stimulation according to a program at a lower battery voltage level.

FIG. 6 is a flow diagram illustrating another example method of determining whether medical device 4 will be able to support the selected therapy program throughout the useable life of power source 34. The method of FIG. 6 is described as being performed by processor 30 of medical device 4. However, in other examples, one or more aspects of the method may additionally or alternatively be performed by a processor or other component of one or both of programmers 20, 22, or a local or remote computing device or server in communication with medical device 4 and/or one or both of programmers 20, 22.

As described with respect to FIG. 5, processor 30 may determine the expected change in voltage level of power source 34 as power source 34 depletes from its present voltage level to a lower voltage level (70). Additionally, charge pump 44 may, under control of processor 30, accumulate energy from power source 34 for delivery of a stimulation signal, e.g., pulse (74). Once charge pump 44 builds up enough charge to generate the stimulation output according to the program selected for therapy delivery (76), e.g., as indicated by system monitor 45, processor 30 may control charge pump to stop charging (78). Processor 30 may determine the duty cycle of charge pump 44 at the present voltage level of power source 34 based on how long charge pump 44 ran to accumulate enough charge to deliver a pulse and the time interval 64 between pulses 62 (80).

Memory 32 may store information regarding how the rate at which charge pump 44 accumulates charge, i.e., charge per time, varies with the voltage level of power source 34. For example, memory 32 may store information regarding a mathematical relationship between the rate at which charge pump 44 accumulates charge and the voltage level of power source 34. The relationship between the rate of charge accumulation of charge pump 44 and change in the voltage level of power source 34 may be linear. For example, if the voltage level of power source 34 decreases by ten percent, the rate at which charge pump 44 accumulates charge from power source 34 may also decrease by ten percent. Consequentially, charge pump 44 may run for ten percent longer to accumulate the same amount of charge. In other examples, memory 32 may include a look-up table or function that defines a relationship between various voltage levels of power source 34 and charge accumulation rates of charge pump 44. The data included in the look-up table or the function may be based on testing using medical device 4 or another medical device.

Based on information regarding how the rate at which charge pump 44 accumulates charge varies with the voltage level of power source 34, processor 30 may determine the duty cycle at the lower voltage level of power source 34 (90). For example, processor 30 may access information regarding relationships between various voltage levels of power source 34 and charge accumulation rates of charge pump 44 from memory 32 to determine the duty cycle of charge pump 44 at the lower voltage level of power source 34. In some examples, processor 30 may use the expected change in the voltage level of power source 34 (70) in combination with the information stored in memory 32 to determine the duty cycle of charge pump 44 at the lower voltage level of power source 34. For example, memory 32 may store information regarding how changes in the voltage level of power source 34, e.g., a percent change and/or absolute change, alter the rate at which charge pump 44 accumulates charge, and processor 30 may access the information to determine the duty cycle of charge pump 44 at the lower voltage level of power source 34.

In some examples, processor 30 may calculate the duty cycle at the lower voltage level of power source 34 based on the duty cycle at the present voltage level of power source 34 and information regarding the change in the rate at which charge pump 44 accumulates charge. If the duty cycle at the lower voltage level of power source 34 is greater than one hundred percent, i.e., the charge time required by charge pump 44 is greater than the time interval 64 between pulses 62 (92), processor 30 determines that medical device 4 will be unable to deliver stimulation according to the selected program at the lower voltage level of power source 34 (84).

In response to the determination that medical device 4 will not be able to correctly deliver the stimulation specified by the selected program at the lower battery voltage level, processor 30 may control telemetry module 36 to deliver an alert to a user, e.g., by controlling telemetry module 36 to transmit an indication or information to one or both of programming devices 20, 22, in the manner discussed above (86). As discussed above, programming device may also provide recommendations to the user about how to avoid ineffective stimulation as power source 34 depletes, e.g., by suggesting a decrease in the intensity of stimulation, recharging power source 34 before its charge level reaches a specified lower power source voltage level, replacing power source 34 or medical device 4 when its voltage depletes to a certain value, or the like. As one example, processor 30 may suggest a decreased pulse rate to increase the time between pulses, which may result in the charging time required by charge pump 44 at the lower voltage level of power source 34 being less than, i.e., fitting within, the time between stimulation pulses.

In some examples, processor 30 may reconfigure a minimum voltage level of power source 34 based on the determination that the medical device will be unable to deliver therapy according to the selected program at the lower battery voltage level. For example, processor 30 may inform a user of a programming device, e.g., programming device 20 or 22, or another external device that the medical device will be unable to deliver therapy according to the selected program at a lower battery voltage level via telemetry module 36. In addition to the indication that the medical device will be unable to deliver therapy according to the selected program at the lower power source voltage level, the external device may provide recommendations to the user about how to respond, e.g., decrease an intensity of stimulation, recharge the power source more frequently, or the like. In addition to or instead of such recommendations, the external device may suggest reconfiguring the minimum voltage level of power source 34, such that power source 34 is replaced or recharged prior to reaching the lower power source voltage level.

Processor 30 may suggest a new minimum voltage level of power source 34 based on the information relating the voltage level of power source 34 to the rate of charge accumulation of charge pump 44. For example, processor 30 may determine a maximum allowable change in voltage level of power source 34, e.g., percent change or absolute change, given the information stored in memory 32. The new minimum voltage level of power source 34 may correspond to a voltage level in which the duty cycle of charge pump 44 approaches one hundred percent, i.e., the charge time required by charge pump 44 approaches the time interval 64 between pulses 62. As described in further detail with respect to FIG. 8, in examples in which power source 34 is rechargeable, the external device may display a recharge frequency necessary to prevent the selected program from falling out of regulation.

Although FIG. 6 describes determining a duty cycle at the lower voltage level of power source 34, processor 30 may determine other metrics to evaluate if medical device 4 will be able to deliver stimulation according to the selected program at the lower voltage level of power source 34. For example, processor 30 may determine the rate at which charge pump 44 accumulates charge at the lower voltage level of power source 34 based on information stored in memory 32. Processor 30 may also determine the minimum rate at which charge pump 44 must accumulate charge in order support the selected stimulation program by, for example, dividing the voltage that charge pump 44 must supply to the active regulator module 50, i.e., the sum of the stimulation output and the required headroom of active regulator module 50, by the maximum available charge time between pulses 62, e.g., time interval 64, or interval 64 reduced by any time needed to set up electrical contact module 58 or other components of stimulation interface 46 for delivery of a pulse. Processor 30 may compare the rate at which charge pump 44 accumulates charge at the lower voltage level of power source 34 to the minimum rate at which charge pump 44 must accumulate charge in order support the selected stimulation program to determine whether medical device 4 will be able to deliver stimulation according to the selected program at the lower voltage level of power source 34.

In some examples, the analysis to determine whether medical device 4 is, or will be, unable to deliver stimulation according to the selected program may be performed during a programming session by a clinician, e.g., using clinician programmer 20. The analysis may be performed during testing of new programs or modified programs during such a programming session. Based on the results of such analysis, the clinician may choose programs that medical device 4 will be able to support throughout the useable life of power source 34.

The delivery of ineffective stimulation may be prevented by determining whether a medical device will continue to be able to deliver stimulation as specified by a stimulation program as power source 34 depletes. This may be particularly important for patients receiving stimulation for movement disorders. Some of these patients may become physically disabled if the stimulation intensity is less than is necessary for effective reduction of movement disorder symptoms, making it difficult to correct the situation. If stimulation stops working properly for a patient receiving pain therapy, the patient may be able to alert the clinician, recharge the power source, etc. In contrast, if stimulation stops working properly for a movement disorder patient, the patient may be unable to do so. Additionally, a patient receiving pain therapy may feel tingling sensations during stimulation delivery and notice when the stimulation is interrupted. A patient receiving DBS to treat a movement disorder may not notice that stimulation has been interrupted until symptoms occur, at which point the patient may be unable to correct the situation.

As previously described, in some examples, each electrode of a lead 10 may be associated with a respective voltage or current source, e.g., voltage regulator and/or current regulator. Accordingly, in some examples, selection of electrodes and polarities by processor 30 according to an electrode configuration specified in a stimulation program may involve selection of a voltage or current source by the processor, instead of or in addition to switching the source across selected electrodes. For example, in examples in which medical device 4 may deliver either constant voltage or constant current stimulation, voltage regulator module 50A may include a voltage regulator for each electrode of a lead 10, and current regulator module 50B may provide a current regulator for each electrode of a lead 10.

Figure 7:
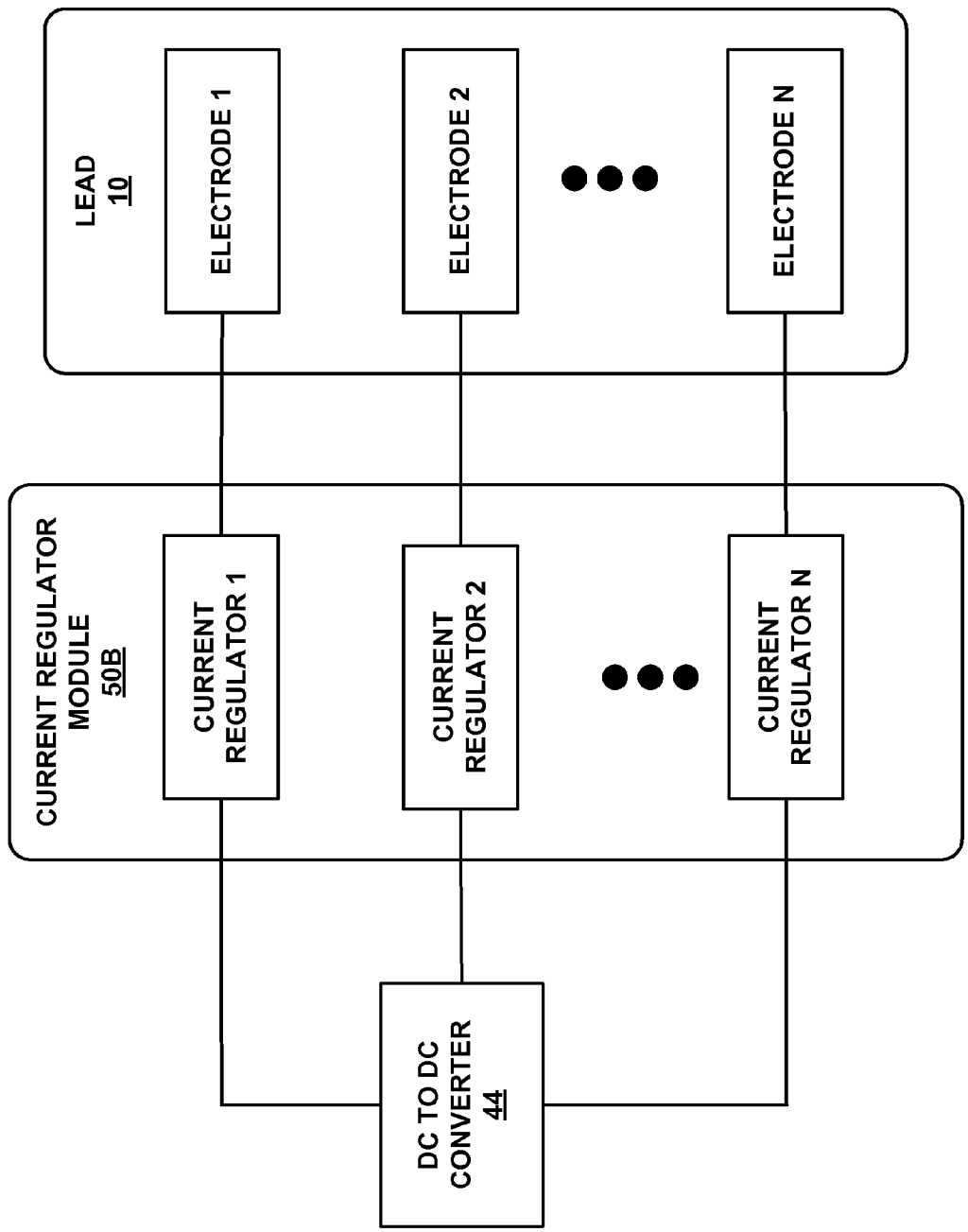
FIG. 7 illustrates an example configuration of a stimulation interface in which each electrode of a lead is associated with a respective current regulator.

FIG. 7 illustrates an example configuration in which each electrode of lead 10 is associated with a respective current regulator to deliver stimulation at a constant current. Lead 10 may include any number of electrodes, and regulator module 50B may include a regulator for each electrode such that one regulator is associated with each electrode of lead 10.

In the example illustrated by FIG. 7, therapy is delivered to patient 6 at a constant current. However, this disclosure is not limited to using multiple current sources to deliver therapy at a constant current. In other examples, each electrode of a lead 10 may be associated with a respective voltage and/or current source, e.g., voltage regulator and/or current regulator, to deliver therapy at a constant voltage and/or constant current.

In the constant current stimulation example illustrated in FIG. 7, the regulators of regulator module 50B may each output a constant current to lead 10 at an amplitude specified by a stimulation program, based on a digital input from processor 30. For example, processor 30 may specify which electrodes of lead 10 will be activated to deliver stimulation and also the polarities of the active electrodes.

Figure 8:
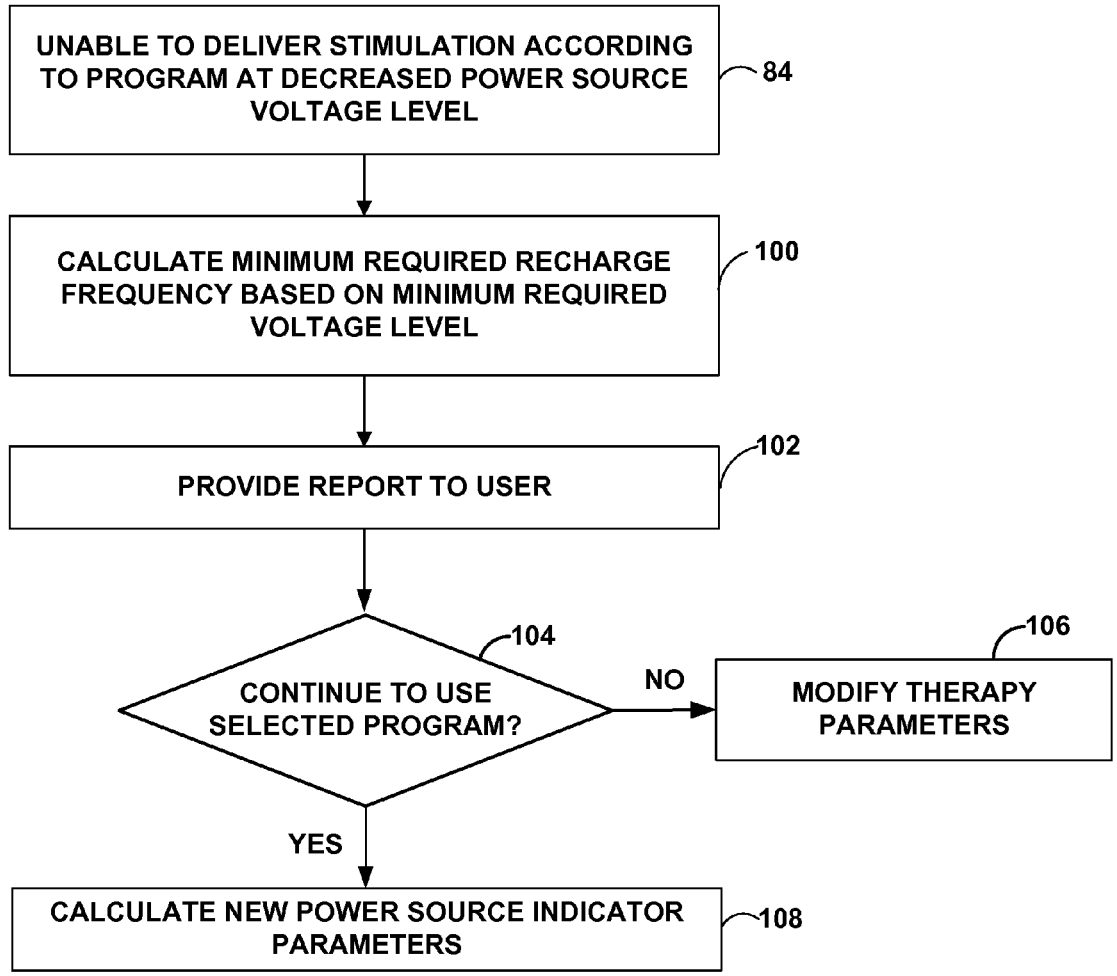
FIG. 8 is a flow diagram illustrating an example method of reconfiguring a minimum voltage level of a power source.

FIG. 8 is a flow diagram illustrating an example method of reconfiguring a minimum voltage level of power source 34. Although FIG. 8 is primarily described with respect to examples in which power source 34 is rechargeable, in other examples, a minimum voltage level of a non-rechargeable power source may be reconfigured.

As described with respect to FIGS. 5 and 6, processor 30 determines that medical device 4 will be unable to deliver stimulation according to the selected program at the lower voltage level of power source 34 (84). Based on this determination, processor 30 or a processor of an external device, e.g., programmer 20 or 22, may calculate the minimum recharge frequency required to prevent the selected program from falling out of regulation (100). The minimum required recharge frequency may be based on the minimum voltage level of power source 34 necessary to ensure charge pump 44 will be able to charge to a level required by the selected therapy program during the time interval 64 between pulses 62, e.g., the new minimum voltage level suggested by processor 30, as described with respect to FIGS. 5 and 6. For example, the minimum required recharge frequency may be the recharge frequency required to prevent the voltage level of power source 34 from falling below the new minimum voltage suggested by processor 30.

In examples in which power source 34 is non-rechargeable, processor 30 or a processor of an external device may calculate a modified power source replacement schedule. For example, processor 30 may calculate how much earlier power source 34 would need to be replaced if the selected therapy program were used for therapy delivery. The modified replacement schedule may be based on the minimum required voltage level of power source 34. For example, power source 34 may need to be replaced prior to depleting to the minimum required voltage level.

The external device, e.g., programmer 20 or 22, may display a report to a user specifying the minimum required recharge frequency (102). For example, processor 30 may control telemetry module 36 to provide the report to the external device. The report may also include an indication that the medical device may be unable to deliver stimulation according to selected program at the lower power source voltage level. In some examples, the report may provide recommendations to a user based on how much the minimum required recharge frequency for the selected program compares to the recharge frequency typically used when power source 34 is allowed to deplete to the lower power source voltage level. For example, if the minimum required recharge frequency for the selected program substantially varies from the recharge frequency typically used when power source 34 is allowed to deplete to the lower power source voltage level, the report may suggest decreasing the stimulation intensity instead of modifying the recharge frequency.

A user may decide whether to continue using the selected program (104). If the user does not chose to continue therapy delivery using the selected program, the therapy parameters may be modified (106). For example, a user may decrease the stimulation intensity of the selected program or select a new program, e.g., via programming device 20 or 22.

If the user decides to continue using the selected program for therapy delivery, the power source voltage level indicator parameters may be reconfigured (108). Programming device 20 and/or programming device 22 may display an indicator of the present voltage level of power source 34. The power source voltage level indicator allows the user to determine when power source 34 requires recharging. The gauge of the power source voltage indicator may be resealed to reflect the minimum required recharge frequency associated with the selected program.

In some examples, the power source voltage indicator includes markings to indicate that the power source voltage level is at a maximum, three fourths of the maximum, one half of the maximum, one fourth of the maximum, and a minimum. The minimum voltage level displayed on the gauge may be set, for example, to the minimum voltage level of power source 34 necessary to ensure the active regulator module 50 will be able to produce the desired output according to the selected therapy program. Likewise, the half and quarter markings may be recalculated to reflect the new minimum voltage level of power source 34.

Various examples have been described. One of ordinary skill in the art will understand that various modifications may be made to the described examples without departing from the scope of the inventions defined by the claims. For example, although described with reference to examples in which a voltage or current source for delivery of stimulation includes a voltage regulator, other examples may additionally or alternatively include a current regulator. These and other examples are within the scope of the following claims.

The invention claimed is:

1. A method comprising:
   determining a length of time a charge pump charged at a present voltage level of a power source to reach a level of charge on the charge pump sufficient to provide a stimulation output according to a stimulation program;
   determining a total time interval available for the charge pump to charge during delivery of stimulation according to the stimulation program; and
   determining whether a medical device will be able to deliver stimulation according to the program at a voltage level of the power source that is lower than the present voltage level of the power source based on the length of time the charge pump charged at the present voltage level of the power source and the total time interval available for the charge pump to charge.

2. The method of claim 1,
   further comprising determining a duty cycle of the charge pump at the present voltage level of the power source based on the length of time the charge pump charged and the total time interval available for the charge pump to charge,
   wherein determining whether the medical device will be able to deliver stimulation according to the program at the voltage level of the power source that is lower than the present voltage level comprises determining whether the medical device will be able to deliver stimulation according to the program at the voltage level of the power source that is lower than the present voltage level based on the duty cycle.

3. The method of claim 2,
   further comprising comparing the duty cycle to a threshold value,
   wherein determining whether the medical device will be able to deliver stimulation comprises determining whether the medical device will be able to deliver stimulation according to the program at the voltage level of the power source that is lower than the present voltage level of a power source based on the comparison.

4. The method of claim 3, further comprising:
   determining a difference between the present voltage level and the lower voltage level; and
   determining the threshold value based on the difference.

5. The method of claim 2, further comprising:
   accessing information regarding a change in a rate at which the charge pump accumulates charge as the power source depletes from the present voltage level to the lower voltage level; and
   calculating a duty cycle of the charge pump at the lower voltage level of the power source based on the duty cycle of the charge pump at the present voltage level of the power source and the information regarding the change in the rate at which charge pump accumulates charge,
   wherein determining whether the medical device will be able to deliver stimulation comprises determining whether the medical device will be able to deliver stimulation according to the program at the lower voltage level of the power source based on the duty cycle of the charge pump at the lower voltage level of the power source.

6. The method of claim 1, wherein determining whether the medical device will be able to deliver stimulation according to the program at the lower power source voltage level comprises determining whether the medical device will be able to deliver stimulation according to the program at the lower power source voltage level in response to receipt of the program.

7. The method of claim 1, wherein determining whether the medical device will be able to deliver stimulation according to the program at the lower power source voltage level comprises determining whether the medical device will be able to deliver stimulation according to the program at the lower power source voltage level in response to modification of the program.

8. The method of claim 1, further comprising providing an indication to a user of whether the medical device is able to deliver electrical stimulation according to the program at the lower power source voltage level based on the determination.

9. The method of claim 8 wherein providing the indication comprises sending the indication to a programming device, wherein the programming device presents the indication to the user.

10. The method of claim 8 wherein the indication comprises an indication that the medical device is not able to deliver electrical stimulation according to the program at the lower power source voltage level, wherein the power source comprises a rechargeable power source, and wherein the indication further comprises a minimum recharge frequency required for the program.

11. The method of claim 10 further comprising resealing a gauge of a power source voltage level indicator based on the minimum recharge frequency required for the program.

12. The method of claim 8 wherein the indication comprises an indication that the medical device is not able to deliver electrical stimulation according to the program at the lower power source voltage level, wherein the power source comprises a non-rechargeable power source, and wherein the indication further comprises a modified power source replacement schedule required for the program.

13. The method of claim 1, wherein determining the total time interval available for the charge pump to charge during delivery of stimulation according to the stimulation program comprises determining a time interval between stimulation pulses of the stimulation program.

14. The method of claim 1, wherein determining the total time interval available for the charge pump to charge during delivery of stimulation according to the stimulation program comprises determining a time interval between stimulation pulses of the stimulation program and a pulse duration of one of the stimulation pulses of the stimulation program.

15. A medical device system comprising:
   a medical device comprising:
      a power source at a present power source voltage level, and
      a signal generator that generates electrical stimulation, wherein the signal generator comprises a charge pump coupled to the power source; and
   a processor that determines a length of time that the charge pump charged at the present power source voltage level to reach a level of charge on the charge pump sufficient to provide a stimulation output according to a stimulation program, determines a total time interval available for the charge pump to charge during delivery of stimulation according to the stimulation program, and determines whether the medical device will be able to deliver stimulation according to the program at a voltage level of the power source that is lower than the present voltage level of the power source based on the length of time the charge pump charged at the present voltage level of the power source and the total time interval available for the charge pump to charge.

16. The system of claim 15, wherein the processor determines a duty cycle of the charge pump for the present voltage level of the power source based on the length of time the charge pump charges and the time between stimulation pulses, and determines whether the medical device will be able to deliver stimulation according to the program at the voltage level of the power source that is lower than the present voltage level based on the duty cycle.

17. The system of claim 16, wherein the processor compares the duty cycle to a threshold value, and determines whether the medical device will be able to deliver stimulation according to the program at the power source voltage level lower than the present voltage level of a power source based on the comparison.

18. The system of claim 17, wherein the processor calculates a difference between the present power source voltage level and the lower power source voltage level, and determines the threshold value based on the difference.

19. The system of claim 16, wherein the processor accesses information regarding a change in a rate at which the charge pump accumulates charge as the power source depletes from the present voltage level to the lower voltage level, calculates a duty cycle of the charge pump for the lower voltage level of the power source based on the duty cycle of the charge pump for the present voltage level of the power source and the information regarding the change in the rate at which charge pump accumulates charge, and determines whether the medical device will be able to deliver stimulation according to the program at the lower power source voltage level based on duty cycle of the charge pump at the lower voltage level of the power source.

20. The system of claim 15, wherein the processor provides an indication via the transceiver of whether the medical device will be able to deliver stimulation according to the program at the lower power source voltage level.

21. The system of claim 20, wherein the indication comprises an indication that the medical device is not able to deliver electrical stimulation according to the program at the lower power source voltage level, wherein the power source comprises a rechargeable power source, and wherein the indication further comprises a minimum recharge frequency required for the program.

22. The system of claim 21, wherein the processor rescales a gauge of a power source voltage level indicator based on the minimum recharge frequency required for the program.

23. The system of claim 20, wherein the indication comprises an indication that the medical device is not able to deliver electrical stimulation according to the program at the lower power source voltage level, wherein the power source comprises a non-rechargeable power source, and wherein the indication further comprises a modified power source replacement schedule required for the program.

24. The system of claim 20, further comprising a transceiver, wherein the processor provides the indication to an external programming device via the transceiver.

25. The system of claim 15, wherein the medical device comprises an implantable medical device.

26. The system of claim 15, wherein the power source comprises a battery.

27. The system of claim 15, wherein the power source is rechargeable.

28. The system of claim 15, wherein the lower power source voltage level comprises a minimum threshold voltage of the power source below which therapy delivery by the medical device will cease.

29. The system of claim 15, wherein the processor comprises a processor of the medical device.

30. The system of claim 15, wherein the processor determines the total time interval available for the charge pump to charge during delivery of stimulation according to the stimulation program as a time interval between stimulation pulses of the stimulation program.

31. The system of claim 15, wherein the processor determines the total time interval available for the charge pump to charge during delivery of stimulation according to the stimulation program as a time interval between stimulation pulses of the stimulation program and a pulse duration of one of the stimulation pulses of the stimulation program.

32. A medical device system comprising:
 means for determining a length of time a charge pump charged at a present voltage level of a power source to reach a level of charge on the charge pump sufficient to provide a stimulation output according to a stimulation program;
 means for determining a total time interval available for the charge pump to charge; and
 means for determining whether the medical device will be able to deliver stimulation according to the program at a power source voltage level lower than a present voltage level of a power source based on the length of time the charge pump charges at the present voltage level of the power source and the total time interval available for the charge pump to charge.

* * * * *